(12) United States Patent
Thompson

(10) Patent No.: US 12,415,850 B2
(45) Date of Patent: *Sep. 16, 2025

(54) COMPOSITIONS AND METHODS FOR REGULATING PRODUCTION OF AN ANTIBODY LIKE PROTEIN AND RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

(*) Notice: Subject to any disclaimer, the term of this patent is extended or adjusted under 35 U.S.C. 154(b) by 0 days.

This patent is subject to a terminal disclaimer.

(21) Appl. No.: 18/432,991

(22) Filed: Feb. 5, 2024

(65) Prior Publication Data

US 2025/0051424 A1 Feb. 13, 2025

Related U.S. Application Data

(63) Continuation of application No. 18/446,965, filed on Aug. 9, 2023, now Pat. No. 12,162,927.

(51) Int. Cl.
| | |
|---|---|
| *C12N 15/86* | (2006.01) |
| *A61P 31/16* | (2006.01) |
| *C07K 16/10* | (2006.01) |
| *C12N 15/113* | (2010.01) |

(52) U.S. Cl.
CPC .......... *C07K 16/1018* (2013.01); *A61P 31/16* (2018.01); *C12N 15/113* (2013.01); *C12N 15/86* (2013.01); *C12N 2310/141* (2013.01); *C12N 2750/00043* (2013.01)

(58) Field of Classification Search
None
See application file for complete search history.

(56) References Cited

U.S. PATENT DOCUMENTS

| | | |
|---|---|---|
| 11,085,055 B2 | 8/2021 | Mallol et al. |
| 11,162,102 B2 | 11/2021 | Minshull et al. |
| 11,530,423 B1 | 12/2022 | Thompson |
| 11,873,505 B2 | 1/2024 | Thompson |
| 12,018,274 B2 | 6/2024 | Thompson |
| 12,134,770 B1 | 11/2024 | Thompson |
| 2020/0188456 A1* | 6/2020 | Weinstein .............. C12N 15/86 |
| 2024/0026377 A1 | 1/2024 | Thompson |

FOREIGN PATENT DOCUMENTS

CA  2721333 A1  10/2009

OTHER PUBLICATIONS

Del Rosario, et al. Front Immunol. May 29, 2020;11:627. doi: 10.3389/fimmu.2020.00627. PMID: 32547534. (Year: 2020).*
Tang, et al. Mol Ther Nucleic Acids. Apr. 19, 2016;5(4):e311. doi: 10.1038/mtna.2016.25. PMID: 27093169. (Year: 2016).*
O'Brien et al. "Overview of microRNA biogenesis, mechanisms of actions, and circulation." Frontiers in endocrinology 9 (2018): 402.
Gorski et al. "RNA-based recognition and targeting: sowing the seeds of specificity." Nature Reviews Molecular Cell Biology 18.4 (2017): 215-228.
Bottoni et al. "Targeting BTK through microRNA in chronic lymphocytic leukemia." Blood, The Journal of the American Society of Hematology 128.26 (2016): 3101-3112.
Christensen et al. "Recombinant adeno-associated virus-mediated microRNA delivery into the postnatal mouse brain reveals a role for miR-134 in dendritogenesis in vivo." Frontiers in neural circuits 3 (2010): 848.
Bofill-De Ros et al. "Guidelines for the optimal design of miRNA-based shRNAs." Methods 103 (2016): 157-166.
Denzler et al. "Impact of microRNA levels, target-site complementarity, and cooperativity on competing endogenous RNA-regulated gene expression." Molecular cell 64.3 (2016): 565-579.
Van Den Berg et al. "Design of effective primary microRNA mimics with different basal stem conformations." Molecular Therapy Nucleic Acids 5 (2016).
Tritschler et al. "Concepts and limitations for learning developmental trajectories from single cell genomics." Development 146.12 (2019): dev170506.
Ahmadzadeh et al. "BRAF mutation in hairy cell leukemia." Oncology reviews 8.2 (2014): 253.
Patton et al. "Biogenesis, delivery, and function of extracellular RNA." Journal of extracellular vesicles 4.1 (2015): 27494.
Clark et al. "Detection of BRAF splicing variants in plasma-derived cell-free nucleic acids and extracellular vesicles of melanoma patients failing targeted therapy therapies." Oncotarget 11.44 (2020): 4016.
Wang et al. "Adeno-associated virus vector as a platform for gene therapy delivery." Nature reviews Drug discovery 18.5 (2019): 358-378.
Kondratov et al. "Direct head-to-head evaluation of recombinant adeno-associated viral vectors manufactured in human versus insect cells." Molecular Therapy 25.12 (2017): 2661-2675.
Nature (2010. Gene Expression. Scitable. Available online at Nature. com) <https://www.nature.com/scitable/topicpage/gene-expression-14121669> (2010).
Brutons Tyrosine Kinase Genbank Sequence (2023).

(Continued)

*Primary Examiner* — Benjamin P Blumel
*Assistant Examiner* — Jeffrey Mark Sifford
(74) *Attorney, Agent, or Firm* — Gowling WLG (Canada) LLP

(57) ABSTRACT

The present disclosure relates to one or more agents, therapies, treatments, and methods of use of the agents and/or therapies and/or treatments for producing an antibody like protein (ALP) and one or more sequences of miRNA that are complementary to the mRNA of a target, viral-specific protein or proteins. Embodiments of the present disclosure can be used as a therapy or a treatment for a subject that has a condition whereby the production of the APL and decreased production of a target, viral-specific protein or proteins may be of therapeutic benefit.

2 Claims, 1 Drawing Sheet

Specification includes a Sequence Listing.

(56) References Cited

OTHER PUBLICATIONS

GenBank EGFR Sequence (2023).
GenBank EGF Sequence (2023).
NCBI search results for SEQ ID No. 5 (2024).
NCBI Nucleotide Sequence ALK Lingand, search performed Dec. 26, 2024 (2023).
NCBI Nucleotide Sequence ALK Receptor, search performed Dec. 26, 2024 (2023).
NCBI Nucleotide Sequence for PARP, search performed Dec. 26, 2024 (2024).
GenBank FLT3 Sequence (2024).
Martinez-Navio, et al. Immunity. Mar. 19, 2019; 50(3):567-575.e5. doi 10.1016/j.immuni.2019.02.005. epub Mar. 5, 2019. PMID: 30850342. (Year: 2019).
Ahluwalia, et al. Retrovirology. Dec. 23, 2008; 5:117. doi: 10118617424690-5-117. PMID: 19102781 (Year: 2008).

* cited by examiner

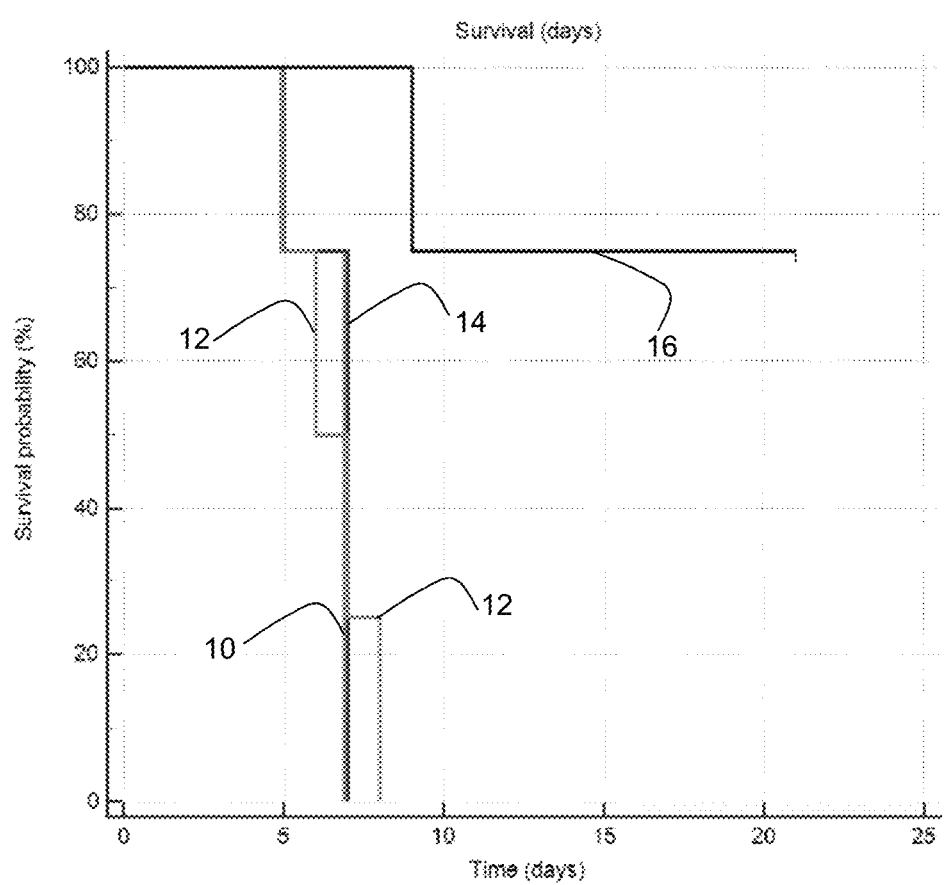

SEQUENCE LISTING

```
Sequence total quantity: 3
SEQ ID NO: 1              moltype = DNA  length = 2340
FEATURE                   Location/Qualifiers
source                    1..2340
                          mol_type = other DNA
```

```
                          organism = synthetic construct
SEQUENCE: 1
ggtaccgcca ccatggctac tgggtcaaga acatctctgc tgctggcttt cgggctgctg    60
tgcctgcctt ggctgcagga ggggagtgct caggtccagc tgcaggagag cggaccaggc   120
ctggtgaagc cttccgagac actgtctctg acctgctccg tgtctggcgt gtccgtgaca   180
tctgacatct actattggac ctggatcagg cagccacctg gcaagggcct ggagtggatc   240
ggctacatct tctataacgg cgacaccaac tacaatccca gcctgaagtc cagagtgaca   300
atgagcatcg atacctccaa gaatgagttc tctctgaggc tgacaagcgt gaccgcagca   360
gacacagccg tgtactttg cgccagggc accgaggatc tgggctattg cagctccggc   420
tcctgtccta accactgggg ccagggcaca ctggtgaccg tgtctagctc cacaaaggc   480
ccaagcgtgt ttcctctggc cccatctagc aagagcacat ccggaggcac cgccgccctg   540
ggatgtctgt tgaaggatta cttcccagag cccgtgaccg tgtcttggaa cagcggcgcc   600
ctgacatccg gagtgcacac cttccagcc gtgctgcagt cctctggcct gtacagcctg   660
agctccgtgg tgacagtgcc ttctagctcc ctgggcacag agacctatat ctgcaacgtg   720
aatcacaagc ccagcaatac caaggtggac aagaaggtgg agcctaagtc ctgtgataag   780
acacacacct gcccaccatg tcctgcacca gagctgctgg gaggaccatc cgtgttcctg   840
ttttctccaa agcccaagga cacactgatg atctctcgca cacccgaggt gacctgcgtg   900
gtggtggacg tgagccacga ggatcctgag gtgaagttca actggtacgt ggatggcgtg   960
gaggtgcaca atgccaagac caagcctaga gaggagcagt acaacagcac atatcgggtg  1020
gtgtccgtgc tgaccgtgct gcaccaggac tggctgaacg gcaaggagta taagtgcaag  1080
gtgtccaata aggccctgcc cgcccctatc gagaagacaa tctctaaggc aaagggacag  1140
ccaagggagc ctcaggtgta cacccctgcc ccttccagg aggagatgac aaagaaccag  1200
gtgtctctga cctgtctggt gaagggcttc tatcccttcg acatcgccgt ggagtgggag  1260
tctaatggcc agcagagaa caattacaag accacaccac ccgtgctgga ctccgatggc  1320
tcttttcttc tgtattctaa gctgaccgtg gataagagca gatggcagca gggcaacgtg  1380
ttttcttgta gcgtgatgca cgaggccctg cacaatcact acacacagaa gtccctgtct  1440
ctgagcccag gcaagaggaa gaggagagca cgaggccctg cacaatcact acacacagaa  1500
gtccctgtct ctgagcccag gcaagaggaa gaggagatcc ggatctggag caccagtgaa  1560
gcagaccctg aacttcgacc tgctgaagct ggccggcgat gtggagagca atccaggccc  1620
catggccaca ggcagcagaa cctccctgct gctggccttt ggctgctgt gcctgccatg  1680
gctgcaggag ggaagcgcc acatccagat gacccagtcc ccatctagcc tgagcgcctc  1740
catcggcgat cgggtgacaa tcacctgtcg cccctcccag aacatcaggt ctttcctgaa  1800
ttggtttcag cacaagccag gcaaggcccc caagctgctg atctacgcag catctaacct  1860
gcagagcggc gtgccatccc gcttctctgg aagcggatcc ggcacagagt ttacactgac  1920
catcagctcc ctgcagcccg aggacttcgc cacctactat tgccagcaga gctataacac  1980
acctccaacc tttggccagg gcacaaaggt ggagatcaag gacagccta aggcagcacc  2040
atccgtgacc ctgttcccac cttcctctga ggagctgcag gccaataagg ccaccctggt  2100
gtgcctgatc agcgacttt accctggagc agtgaccgtg gcatggaagg ccgatagctc  2160
ccctgtgagg cggcgtgga gacaacaacc ccatctaagc agagcaacaa taagtacgcc  2220
gcctctagct atctgtctct gaccccagag cagtggaaga gccaccggtc ttatagctgt  2280
caggtgaccc atgaaggctc aactgtggag aaaaccgtcg ccccaactga atgttcctaa  2340

SEQ ID NO: 2             moltype = DNA  length = 416
FEATURE                  Location/Qualifiers
source                   1..416
                         mol_type = other DNA
                         organism = synthetic construct
SEQUENCE: 2
ctggaggctt gctgaaggct gtatgctgaa ggatcttatt tcttcggaga gttttggcct    60
ctgactgact ttccgaagat aagatccttc aggacacaag gcctgttact agcactcaca   120
tggaacaaat ggcctctagc ctggaggctt gctgaaggct gtatgctgga agcaattgga   180
gagtgcctaa gttttggcct ctgactgact taggcacttc aattgcttcc aggacacaag   240
gcctgttact agcactcaca tggaacaaat ggcctctagc ctggaggctt gctgaaggct   300
gtatgctgtg aagatctgtt ccaccattga gttttggcct ctgactgact taatggtgac   360
agatcttcac aggacacaag gcctgttact agcactcaca tggaacaaat ggcctc       416

SEQ ID NO: 3             moltype = DNA  length = 8529
FEATURE                  Location/Qualifiers
source                   1..8529
                         mol_type = other DNA
                         organism = synthetic construct
SEQUENCE: 3
cagcagctgc gcgctcgctc gctcactgag gccgcccggg caaagcccgg gcgtcgggcg    60
acctttggtc gcccggcctc agtgagcgag cgagcgcgca gagagggagt gccaactcc   120
atcactaggg gttccttgta gttaatgatt aacccgccat gctacttatc tacgtagcca   180
tgctctagga cattgattat tgactagtgg agttccgcgt tacataactt acggtaaatg   240
gcccgcctgg ctgaccgccc aacgacccc gcccattgac gtcaataatg acgtatgttc   300
ccatagtaac gccaataggg actttccatt gacgtcaatg ggtggagtat ttacggtaaa   360
ctgcccactt ggcagtacat caagtgtatc atatgccaag tacgccccct attgacgtca   420
atgacggtaa atggcccgcc tggcattatg cccagtacat gaccttatgg gactttccta   480
cttggcagta catctacgta ttagtcatcg ctattaccat ggtcgaggtg agccccacgt   540
tctgcttcac tctccccatc tcccccccct cccacccccc aattttgtat ttatttattt   600
tttaattatt ttgtgcagcg atggggggg ggggggggg gggcgcgcgc caggcgggc   660
ggggcgggge gagggggcgg gcgggagagt gcggaaggt caatcagag                720
cggcgcgctc cgaaagtttc cttttatggc gaggcggcgg cggcggcggc cctataaaaa   780
gcgaagcgcg cggcgggcgg gagtcgctgc gcgctgcctt cgccccgtgc cccgctccgc   840
cgccgcctcg cgccgcccgc cccggctctg actaccgcgt tactaaaac aggtaagtcc   900
ggcctccgcg ccgggttttg gcgcctcccg cgggcgcccc cctcctcacg cgagcgctg   960
ccacgtcaga cgaagggcgc agcgagcgtc ctgatccttc cgcccggacg ctcaggacag  1020
```

-continued

```
cggcccgctg ctcataagac tcggccttag aaccccagta tcagcagaag gacatttttag  1080
gacgggactt gggtgactct agggcactgg ttttctttcc agagagcgga acaggcgagg  1140
aaaagtagtc ccttctcggc gattctgcgg agggatctcc gtggggcggt gaacgccgat  1200
gatgcctcta ctaaccatgt tcatgttttc ttttttttc tacaggtcct gggtgacgaa  1260
cagggtaccg ccaccatggc tactgggtca agaacatctc tgctgctgcc tttcgggctg  1320
ctgtgcctgc cttggctgca ggaggggagt gctcaggtcc agctgcagga gagcggacca  1380
ggcctggtga agccttccga gacactgtct ctgacctgct ccgtgtctgg cgtgtccgtg  1440
acatctgaca tctactattg gacctggatc aggcagccac ctggcaaggg cctggagtgg  1500
atcggctaca tcttctataa cggcgacacc aactacaatc cagcctgtca gtccagagtg  1560
acaatgagca tcgatacctc caagaatgag ttctctctga ggctgacaag cgtgaccgca  1620
gcagacacag ccgtgtactt ttgcgccagg ggcaccgagg atctgggcta ttgcagctcc  1680
ggctcctgtc ctaaccactg gggccagggc acactggtga ccgtgtctag ctccacaaag  1740
ggcccaagcg tgtttcctct ggccccatct agcaagagca catccggagg caccgccgcc  1800
ctgggatgtc tggtgaagga ttacttccca gagcccgtga ccgtgtcttg gaacagcggc  1860
gccctgacat ccggagtgca cacctttcca gccgtgctgc agtcctcctg gcctgtacagc  1920
ctgagctccg tggtgacagt gccttctagc tccctgggca cacagaccta tatctgcaac  1980
gtgaatcaca agcccagcaa taccaaggtg gacaagaagg tggagcctaa gtcctgtgat  2040
aagacacaca cctgcccacc atgtcctgca ccagagctgc tgggaggacc atccgtgttc  2100
ctgtttcctc caaagcccaa ggacacactg atgatctctc gcacaccga ggtgacctgc  2160
gtggtggtgg acgtgagcca cgaggatcct gaggtgaagt tcaactggta cgtggatggc  2220
gtggaggtgc acaatgccaa gaccaagcct agagaggagc agtacaacag cacatatcgg  2280
gtggtgtccg tgctgaccgt gctgcaccag gactggctga acggcaagga gtataagtgc  2340
aaggtgtcca ataaggccct gcccgcccct atcgagaaga caatctctaa ggcaaaggga  2400
cagccaaggg agcctcaggt gtacaccctg cccccttcca gggaggagat gacaaagaac  2460
caggtgtctc tgacctgtct ggtgaaggc ttctatcctt ccgacatcgc cgtggagtgg  2520
gagtctaatg gccagccaga gaacaattac aagaccaccc caccggtgct ggactccgat  2580
ggctctttct ttctgtattc taagctgacc gtggataaga gcagatggca gcagggcaac  2640
gtgttttctt gtagcgtgat gcacgaggcc ctgcacaatc actacacaca gaagtccctg  2700
tctctgagcc caggcaagag gaagaggaga tccggatctg gagcaccagt gaagcagacc  2760
ctgaacttcg acctgctgaa gctggccggc gatgtggaga gcaatccagg ccccatggcc  2820
acaggcagca gaacctcctc tgctgctggc tttggcctgc tgtgcctgcc atggctgcag  2880
gagggaagcg ccgacatcca gatgacccag tccccatcta gcctgagcgc ctccatcggc  2940
gatcgggtga caatcacctg tcgccctcc cagaacatca gtcttttcct gaattggttt  3000
cagcacaagc caggcaaggc cccaagctg ctgatctacg cagcatctaa cctgcagagc  3060
ggcgtgccat cccgcttctc tggaagcgga tccggacagg tgtttacact gaccatcagc  3120
tccctgcagc ccgaggactt cgccacctac tattgccagc agagctataa cacacctcca  3180
accttggcc agggcacaaa ggtggagatc aagggacagc ctaaggcagc accatccgtg  3240
accctgttcc caccttcctc tgaggagctg caggccaata aggccaccct ggtgtgcctg  3300
atcagcgact ttaccctgg agcagtgacc gtggcatgga aggccgatag ctcccctgtg  3360
aaggccggcg tggagacaac aaccccatct aagcagagca caataagta cgccgcctct  3420
agctatctgt ctctgacccc agagcagtgg aagagccacc ggtcttatag ctgtcaggtg  3480
acccatgaag gctcaactgt ggagaaaacc gtcgccccaa ctgaatgttc ctaatctaga  3540
cgagctcggt acctctagat gctggagct tgctgaaggc tgtatgctga aggatcttat  3600
ttcttcggag agttttggcc tctgactgac tttccgaaga taagatcctt caggacacaa  3660
ggcctgttac tagcactcac atggaacaaa tggcctctag cctggaggct tgctgaaggc  3720
tgtatgctga aagcaattga ggagtgccta agttttggcc tctgactgac ttaggcactt  3780
caattgcttc caggacacaa ggcctgttac tagcactcac atggaacaaa tggcctctag  3840
cctggaggct tgctgaaggc tgtatgctgt gaagatctgt tccaccattg agttttggcc  3900
tctgactgac ttaatggtga cagatcttca caggacacaa ggcctgttac tagcactcac  3960
atggaacaaa tggcctctct agaaagcttc gtctagaata atcaacctct ggattacaaa  4020
atttgtgaaa gattgactgg tattcttaac tatgttgctc cttttacgct atgtggatac  4080
gctgctttaa tgcctttgta tcatgctatt gcttcccgta tggctttcat tttctcctcc  4140
ttgtataaat cctggttgct gtctctttat gaggagttgt ggcccgttgt caggcaacgt  4200
ggcgtggtgt gcactgtgtt tgctgacgca acccccactg gttggggcat tgccaccacc  4260
tgtcagctcc tttccgggac tttcgctttc ccctcccttg ttgccacggc ggaactcatc  4320
gccgcctgcc ttgcccgctg ctggacaggg gctcggctgt tgggcactga caattccgtg  4380
gtgttgtcgg ggaaatcatc gtcctttcct tggctgctcg cctgtgttgc cacctggatt  4440
ctgcgcggga cgtccttctg ctacgtccct tcggccctca atccagcgga ccttccttcc  4500
cgcggcctgc tgcggctct gcggcctctt gccttcgcc tcagacgagt  4560
cggatctccc tttgggccgc ctccccgcct aagcttatcg ataccgtcga gatctaactt  4620
gtttattgca gcttataatg gttacaaata aagcaatagc atcacaaatt tcacaaataa  4680
agcattttttt tcactgcatt ctagttgtgg tttgtccaaa ctcatcaatg tatcttatca  4740
tgtctggatc tcgacctcga ctagagcatg gctacgtaga taagtagcat ggcgggttaa  4800
tcattaacta caaggaaccc tctagtgatgg agttggccac tccctctctg cgcgctcgct  4860
cgctcactga ggccgggcga ccaaaggtcg cccgacgccc gggctttgcc cgggcggcct  4920
cagtgagcga gcgagcgcgc agctggcgta atagcgaaga ggcccgcacc gatcgccctt  4980
cccaacagtt gcgcagcctg aatggcgaat ggcgattccg ttgcaatggc tggcggtaat  5040
attgttctgg atattaccag caaggccgat agtttgagtt cttctactca ggcaagtgat  5100
gttattacta atcaaagaag tattgctgaca acggttaatt tgcgtgatgg acagactctt  5160
ttactcggtg gcctcactga ttataaaac acttctcagg attctggcgt accgttcctg  5220
tctaaaatcc ctttaatcgg cctcctgttt agctcccgct ctgattctaa cgaggaaagc  5280
acgttatacg tgctcgtcaa agcaaccata gtacgcgccc tgtagcggcg cattaagcgc  5340
ggcgggtgtg tggttacgc gcagcgtgac cgctacactt gccagcgccc tagcgcccgc  5400
tcctttcgct ttcttccctt cctttctcgc cacgttcgcc gtcaagctct  5460
aaatcggggg ctccctttag ggttccgatt tagtgcttta cggcacctcg accccaaaaa  5520
acttgattag ggtgatggtt cacgtagtgg gccatcgccc tgatagacgg ttttcgccc  5580
tttgacgttg gagtccacgt tctttaatag tggactcttg ttccaaactg gaacaacact  5640
caaccctatc tcggtctatt cttttgattt ataagggatt ttgccgattt cggcctattg  5700
gttaaaaaat gagctgattt aacaaaaatt taacgcgaat ttaacaaaaa tattaacgtt  5760
```

-continued

```
tacaatttaa atatttgctt atacaatctt cctgtttttg gggcttttct gattatcaac 5820
cggggtacat atgattgaca tgctagtttt acgattaccg ttcatcgatt ctcttgtttg 5880
ctccagactc tcaggcaatg acctgatagc ctttgtagag acctctcaaa aatagctacc 5940
ctctccggca tgaatttatc agctagaacg gttgaatatc atattgatgg tgatttgact 6000
gtctccggcc tttctcaccc gtttgaatct ttacctacac attactcagg cattgcattt 6060
aaaatatatg agggttctaa aaattttat ccttgcgttg aaataaaggc ttctcccgca 6120
aaagtattac agggtcataa tgtttttggt acaaccgatt tagctttatg ctctgaggct 6180
ttattgctta attttgctaa ttctttgcct tgcctgtatg atttattgga tgttggaatt 6240
cctgatgcgg tattttctcc ttacgcatct gtgcggtatt tcacaccgca tatggtgcac 6300
tctcagtaca atctgctctg atgccgcata gttaagccag ccccgacacc cgccaacacc 6360
cgctgacgcg ccctgacggg cttgtctgct cccggcatcc gcttacagac aagctgtgac 6420
cgtctccggg agctgcatgt gtcagaggtt ttcaccgtca tcaccgaaac gcgcgagacg 6480
aaagggcctc gtgatacgcc tatttttata ggttaatgtc atgataataa tggtttctta 6540
gacgtcaggt ggcactttc ggggaaatgt gcgcggaacc cctatttgtt tatttttcta 6600
aatacattca aatatgtatc cgctcatgag acaataaccc tgataaatgc ttcaataata 6660
ttgaaaaagg aagagtatga gtattcaaca tttccgtgtc gcccttattc ccttttttgc 6720
ggcattttgc cttcctgttt ttgctcaccc agaaacgctg gtgaaagtaa aagatgctga 6780
agatcagttg ggtgcacgag tgggttacat cgaactggat ctcaacagcg gtaagatcct 6840
tgagagtttt cgccccgaag aacgttttcc aatgatgagc acttttaaag ttctgctatg 6900
tggcgcggta ttatcccgta ttgacgccgg gcaagagcaa ctcggtcgcc gcatacacta 6960
ttctcagaat gacttggttg agtactcacc agtcacagaa aagcatctta cggatggcat 7020
gacagtaaga gaattatgca gtgctgccat aaccatgagt gataacactg cggccaactt 7080
acttctgaca acgatcggag gaccgaagga gctaaccgct tttttgcaca acatggggga 7140
tcatgtaact cgccttgatc gttgggaacc ggagctgaat gaagccatac caaacgacga 7200
gcgtgacacc acgatgcctg tagcaatggc aacaacgttg cgcaaactat taactggcga 7260
actacttact ctagcttccc ggcaacaatt aatagactgg atggaggcgg ataaagttgc 7320
aggaccactt ctgcgctcgg cccttccggc tggctggttt attgctgata aatctggagc 7380
cggtgagcgt gggtctcgcg gtatcattgc agcactgggg ccagatggta agccctcccg 7440
tatcgtagtt atctacacga cggggagtca ggcaactatg gatgaacgaa atagacagat 7500
cgctgagata ggtgcctcac tgattaagca ttggtaactg tcagaccaag tttactcata 7560
tatactttag attgatttaa aacttcattt ttaatttaaa aggatctagg tgaagatcct 7620
ttttgataat ctcatgacca aaatccctta acgtgagttt tcgttccact gagcgtcaga 7680
ccccgtagaa aagatcaaag gatcttcttg agatcctttt tttctgcgcg taatctgctg 7740
cttgcaaaca aaaaaaccac cgctaccagc ggtggtttgt ttgccggatc aagagctacc 7800
aactcttttt ccgaaggtaa ctggcttcag cagagcgcag ataccaaata ctgtccttct 7860
agtgtagccg tagttaggcc accacttcaa gaactctgta gcaccgccta catacctcgc 7920
tctgctaatc ctgttaccag tggctgctgc cagtggcgat aagtcgtgtc ttaccgggtt 7980
ggactcaaga cgatagttac cggataaggc gcagcggtcg ggctgaacgg ggggttcgtg 8040
cacacagccc agcttggagc gaacgaccta caccgaactg agatacctac agcgtgagct 8100
atgagaaagc gccacgcttc ccgaagggag aaaggcggac aggtatccgg taagcggcag 8160
ggtcggaaca ggagagcgca cgagggagct tccaggggga aacgcctggt atctttatag 8220
tcctgtcggg tttcgccacc tctgacttga gcgtcgattt ttgtgatgct cgtcaggggg 8280
gcggagccta tggaaaaacg ccagcaacgc ggcctttta cggttcctgg ccttttgctg 8340
gccttttgct cacatgttct ttcctgcgtt atcccctgat tctgtggata accgtattac 8400
cgcctttgag tgagctgata ccgctcgccg cagccgaacg accgagcgca gcgagtcagt 8460
gagcgaggaa gcggaagagc gcccaatacg caaaccgcct ctccccgcgc gttggccgat 8520
tcattaatg                                                        8529
```

COMPOSITIONS AND METHODS FOR REGULATING PRODUCTION OF AN ANTIBODY LIKE PROTEIN AND RIBONUCLEIC ACID

CROSS REFERENCE TO RELATED APPLICATION

The application is a continuation filing and claims the benefit of U.S. Provisional Patent Application Ser. No. 18/446,965, filed Aug. 8, 2023, the entire contents thereof are incorporated herein by reference.

SEQUENCE LISTING

This application contains a Sequence Listing electronically submitted via Patent Center to the United States Patent and Trademark Office as an XML Document file entitled "A8148706US—ST26.xml" created on 2023 Aug. 8 and having a size of 14,542 bytes. The information contained in the Sequence Listing is incorporated by reference herein.

TECHNICAL FIELD

The present disclosure generally relates to compositions and methods for regulating production of an antibody-like protein (ALP) and ribonucleic acid (RNA). In particular, the present disclosure relates to compositions and methods for regulating gene expression and, therefore, production of an ALP and interfering RNA (iRNA), which may suppress viral infections.

BACKGROUND

Viral infections cause mortality in patients. In particular, viral infections affect patients with suppressed immune systems, for example resulting from illness or aging.

It may be desirable to improve therapies and treatments for patients with viral infections.

SUMMARY

Some embodiments of the present disclosure relate to compositions and methods that upregulate the production of both an antibody-like protein (ALP) that targets a surface protein of a virus and one or more sequences of micro-interfering RNA (miRNA) that is complimentary to and degrades, or causes degradation of, mRNA of a target, viral-specific protein or proteins.

In some embodiments of the present disclosure, the target virus is an influenza A virus. In some embodiments of the present disclosure, the target viral-specific protein is an influenza A virus protein or proteins. Without being bound by any particular theory, the ALP can recognize and bind to one or more surface proteins of the target virus, for example influenza A.

In some embodiments of the present disclosure, the composition comprises a plasmid of deoxyribonucleic acid (DNA) that includes an insert sequence of nucleic acids that encode for the production of the ALP, one or more an insert sequences of nucleic acids that encode for the production of miRNA and a backbone sequence of nucleic acids that facilitate introduction of the insert sequence into one or more of a subject's cells where the insert sequence is expressed and/or replicated. Expression of the insert sequence by one or more cells of the subject results in production of the ALP and production of the miRNA. The production of the ALP within one or more of the subject's cells can then bioactivate, recognize and bind to a surface protein of the infecting virus. The production of miRNA within one or more of the subject's cell may result in decreased translation of a target, viral-specific protein by one or more of the subject's cells.

In some embodiments of the present disclosure, the methods that upregulate the production of the ALP and the one or more miRNA sequences also relate to methods of manufacturing and administering the composition.

Some embodiments of the present disclosure relate to a pharmaceutical agent that comprises an agent, and/or a pharmaceutically acceptable carrier. Administering the pharmaceutical agent to a subject may increase the subject's production of the ALP, and one or more sequences of miRNA that decreases the production of a viral specific protein or proteins.

Some embodiments of the present disclosure relate to compositions and methods that can be used as a therapy or a treatment for a viral infection in a subject.

Some embodiments of the present disclosure relate to a method of treating a viral infection. The method comprises a step of administering to a subject a therapeutically effective amount of an agent that upregulates the subject's production of the ALP, and one or more sequences of miRNA that decreases the production of a target, viral-specific protein or proteins.

Embodiments of the present disclosure relate to at least one method for inducing endogenous production of the ALP and one or more sequences of miRNA that target the mRNA of a viral-specific protein or proteins. One such method utilizes gene vectors containing nucleotide sequences for the production of the ALP and one or more sequences of miRNA that target the mRNA of a viral specific protein or proteins, which can be administered to a subject to produce of the ALP and one or more sequences of miRNA. Without being bound by any particular theory, embodiments of the present disclosure may be useful for treating viral infections.

BRIEF DESCRIPTION OF THE DRAWINGS

These and other features of the present disclosure will become more apparent in the following detailed description in which reference is made to the appended drawings.

FIG. 1 is a Kaplan Meier graph of % of animals surviving after infection with influenza A versus time obtained from mice treated with either a control or one of three adeno associated virus (AAV) expression cassettes: one AAV expression cassette with SEQ ID NO: 1; one AAV expression cassette with SEQ ID NO: 2; and, one AAV expression cassette with SEQ ID NO: 3 inserted, according to embodiments of the present disclosure.

DETAILED DESCRIPTION

Unless defined otherwise, all technical and scientific terms used herein have the meanings that would be commonly understood by one of skill in the art in the context of the present description. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

As used herein, the singular forms "a", "an", and "the" include plural references unless the context clearly dictates otherwise. For example, reference to "an agent" includes one or more agents and reference to "a subject" or "the subject" includes one or more subjects.

As used herein, the terms "about" or "approximately" refer to within about 25%, preferably within about 20%, preferably within about 15%, preferably within about 10%, preferably within about 5% of a given value or range. It is understood that such a variation is always included in any given value provided herein, whether or not it is specifically referred to.

As used herein, the term "agent" refers to a substance that, when administered to a subject, causes one or more chemical reactions and/or one or more physical reactions and/or or one or more physiological reactions and/or one or more immunological reactions in the subject. In some embodiments of the present disclosure, the agent is a plasmid, a viral vector containing a plasmid, a protein coat containing a plasmid, or a lipid vesicle containing a plasmid.

As used herein, the term "antibody like protein" refers to proteins that have the same binding properties as "monoclonal antibodies" and may be referred to as "antibody like protein" or "monoclonal antibody" interchangeably.

As used herein, the term "cell" refers to a single cell as well as a plurality of cells or a population of the same cell type or different cell types. Administering an agent to a cell includes in vivo, in vitro and ex vivo administrations and/or combinations thereof.

As used herein, the term "complex" refers to an association, either direct or indirect, between one or more particles of an agent and one or more target cells. This association results in a change in the metabolism of the target cell. As used herein, the phrase "change in metabolism" refers to an increase or a decrease in the one or more target cells' production of DNA, RNA, one or more proteins, and/or any post-translational modifications of one or more proteins.

As used herein, the term "endogenous" refers to the production and/or modification of a molecule that originates within a subject.

As used herein, the terms "inhibit", "inhibiting", and "inhibition" refer to a decrease in activity, response, or other biological parameter of a biologic process, disease, disorder or symptom thereof. This can include but is not limited to the complete ablation of the activity, response, condition, or disease. This may also include, for example, a 10% reduction in the activity, response, condition, or disease as compared to the native or control level. Thus, the reduction can be a 10%, 20%, 30%, 40%, 50%, 60%, 70%, 80%, 90%, 100%, or any amount of reduction in between the specifically recited percentages, as compared to native or control levels.

As used herein, the term "patient" refers to a subject that is afflicted with a disease or disorder. The term "patient" includes human and veterinary subjects.

As used herein, the term "pharmaceutical composition" means any composition comprising, but not necessarily limited to, an agent to be administered a subject in need of therapy or treatment of a disease, disorder or symptom thereof. Pharmaceutical compositions may also additionally include one or more further active ingredients such as antimicrobial agents, anti-inflammatory agents, anaesthetics, analgesics, and the like.

As used herein, the phrases "prevention of" and "preventing" refer to avoiding the onset or progression of a disease, disorder, or a symptom thereof.

As used herein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also be used herein to refer to the functionality of a regulatory molecule, unless the context reasonably indicates otherwise.

As used herein, the terms "promote", "promotion", and "promoting" refer to an increase in an activity, response, condition, disease process, or other biological parameter. This can include, but is not limited to, the initiation of the activity, response, condition, or disease process. This may also include, for example, a 10% increase in the activity, response, condition, or disease as compared to the native or control level. Thus, the increase in an activity, response, condition, disease, or other biological parameter can be 10%, 20%, 30%, 40%, 50%, 60%, 70%, 80%, 90%, 100%, or more, including any amount of increase in between the specifically recited percentages, as compared to native or control levels.

As used herein, the term "subject" refers to any therapeutic target that receives the agent. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue and/or biological fluids.

As used herein, the term "target cell" refers to one or more cells and/or cell types that are deleteriously affected, either directly or indirectly, by a disease process. The term "target cell" also refers to cells that are not deleteriously affected but that are the cells in which it is desired that the agent interacts.

As used herein, the term "therapeutically effective amount" refers to the amount of the agent used that is of sufficient quantity to ameliorate, treat and/or inhibit one or more of a disease, disorder or a symptom thereof. The "therapeutically effective amount" will vary depending on the agent used, the route of administration of the agent and the severity of the disease, disorder or symptom thereof. The subject's age, weight and genetic make-up may also influence the amount of the agent that will be a therapeutically effective amount.

As used herein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used herein, the terms "unit dosage form" and "unit dose" refer to a physically discrete unit that is suitable as a unitary dose for patients. Each unit contains a predetermined quantity of the agent and optionally, one or more suitable pharmaceutically acceptable carriers, one or more excipients, one or more additional active ingredients, or combinations thereof. The amount of agent within each unit is a therapeutically effective amount.

In embodiments of the present disclosure, the pharmaceutical compositions disclosed herein comprise an agent as described above in a total amount by weight of the composition of about 0.1% to about 95%. For example, the amount of the agent by weight of the pharmaceutical composition may be about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%. about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90% or about 95%.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, an agent is a plasmid for introducing genes into a target cell for reproduction or transcription of an insert carried within the plasmid. In some embodiments of the current disclosure, the plasmid is contained in a lipid vesicle, a protein coat, or combinations of both lipid and protein. In some embodiments of the present disclosure, the plasmid is contained within a viral vector. In some embodiments of the present disclosure, the viral vector is an adeno-associated virus (AAV) vector.

In some embodiments of the present disclosure, the insert comprises one or more nucleotide sequences that encode for production of at least an antibody-like protein (ALP) that targets a surface protein of a virus and one or more sequences of micro-interfering RNA (miRNA) each sequence complementary to the mRNA of a target, viral-specific protein or proteins.

In some embodiments of the present disclosure, the ALP targets a surface protein of a virus, such as a coat protein, a spike protein, a membrane fusion protein or a combination thereof of the by recognizing a portion or all of the primary structure (amino acid sequence), the secondary structure (localized protein structures) or the tertiary structure (the three-dimensional shape) of the surface protein. As such, if one or more of the primary, secondary or tertiary structure of a surface protein is known and if that surface protein is accessible by the ALP, then the ALP can target and bind to the given viral protein. Without being bound by any particular theory, the ALP may act in a similar fashion to an antibody. For example, in some embodiments of the present disclosure the ALP may act like a neutralizing antibody and in other embodiments of the present disclosure the ALP may act like a non-neutralizing antibody.

In some embodiments of the present disclosure, the one or more sequences of miRNA are complementary to and, therefore, bind to the target mRNA and cause the target mRNA to be degraded. The degrading of the target mRNA decreases translation of the target mRNA into a resultant target, viral-specific protein.

The present disclosure relates to one or more agents, therapies, treatments, and methods of use of the agents and/or therapies and/or treatments for initiating or upregulating production of the ALP while downregulating production and/or functionality of the target viral protein or proteins. Some embodiments of the present disclosure relate to methods for making a complex between at least one particle of an agent and at least one target cell of a subject for initiating production of the ALP and for downregulating the subject's production and/or functionality of the target, viral-specific protein or proteins. Embodiments of the present disclosure can be used as a therapy or a treatment for a subject that has a viral infection.

In some embodiments of the present disclosure, the agent can be administered to the subject by an intravenous route, an intramuscular route, an intraperitoneal route, an intrathecal route, an intravesical route, a topical route, an intranasal route, a transmucosal route, a pulmonary route, and combinations thereof.

Some embodiments of the present disclosure relate to an agent that can be administered to a subject with a viral infection. When a therapeutically effective amount of the agent is administered to the subject, the subject may produce an ALP and one or more miRNAs that bind to and cause degradation of the mRNA of one or more target, viral-specific proteins.

In some embodiments of the present disclosure, administering a therapeutic amount of the agent to a subject upregulates the production, functionality or both of the ALP and one or more sequences of miRNA that each bind to and cause degradation of the mRNA of one or more target, viral-specific proteins. In some embodiments of the present disclosure, there are one, two or three miRNA sequences that each are complimentary to and degrade, or cause degradation of the mRNA that can be translated into a viral specific protein or proteins.

In some embodiments of the present disclosure, the agent is a vector used for gene therapy. The gene therapy is useful for inducing the subject's endogenous production of the ALP and one or more sequences of miRNA that target the mRNA of a target, viral-specific protein or proteins. For example, the vector can contain one or more nucleotide sequences that that cause production of the ALP and production of one or more miRNA sequences to inhibit a viral infection.

In some embodiments of the present disclosure, the vector used for gene therapy is a virus that can be a double stranded (ds) DNA virus, a single stranded (ss) DNA virus, a ssRNA virus, a dsRNA virus, or combinations thereof.

The embodiments of the present disclosure also relate to administering a therapeutically effective amount of the agent. In some embodiments of the present disclosure, the therapeutically effective amount of the agent that is administered to a patient is between about 10 and about $1 \times 10^{16}$ TCID$_{50}$/kg (50% tissue culture infective dose per kilogram of the patient's body weight). In some embodiments of the present disclosure, the therapeutically effective amount of the agent that is administered to the patient is about $1 \times 10^{13}$ TCID$_{50}$/kg. In some embodiments of the present disclosure, the therapeutically effective amount of the agent that is administered to a patient is measured in TPC/kg (total particle count of the agent per kilogram of the patient's body weight). In some embodiments the therapeutically effective amount of the agent is between about 10 and about $1 \times 10^{16}$ TCP/kg.

Some embodiments of the present disclosure relate to a therapy, or method of treating a viral infection, that can be administered to a subject with the viral infection. The therapy comprises a step of administering to the subject a therapeutically effective amount of an agent that will upregulate the subject's production of the ALP and one or more sequences of miRNA that target the mRNA of a viral-specific protein or proteins. The production of the ALP and production of the miRNA may reduce deleterious effects of the viral infection upon the subject.

The embodiments of the present disclosure relate to assisting subject's experiencing a viral infection. While the examples below relate to influenza A, the following categories include member viruses that are also contemplated as target viruses that are treatable with the embodiments of the present disclosure: a double stranded (ds) DNA virus, a single stranded (ss) DNA virus, a ssRNA virus, a dsRNA virus, or combinations thereof.

Below are examples of nucleotide sequences of each may be present in the insert:

SEQ ID NO: 1 (nucleotide sequence that is codon optimized for ALP-Flu20)

GGTACCGCCACCATGGCTACTGGGTCAAGAACATCTCTGCTGCTGGCTT

TCGGGCTGCTGTGCCTGCCTTGGCTGCAGGAGGGGAGTGCTCAGGTCCA

GCTGCAGGAGAGCGGACCAGGCCTGGTGAAGCCTTCCGAGACACTGTCT

CTGACCTGCTCCGTGTCTGGCGTGTCCGTGACATCTGACATCTACTATT

GGACCTGGATCAGGCAGCCACCTGGCAAGGGCCTGGAGTGGATCGGCTA

CATCTTCTATAACGGCGACACCAACTACAATCCCAGCCTGAAGTCCAGA

GTGACAATGAGCATCGATACCTCCAAGAATGAGTTCTCTCTGAGGCTGA

CAAGCGTGACCGCAGCAGACACAGCCGTGTACTTTTGCGCCAGGGGCAC

CGAGGATCTGGGCTATTGCAGCTCCGGCTCCTGTCCTAACCACTGGGGC

CAGGGCACACTGGTGACCGTGTCTAGCTCCACAAAGGGCCCAAGCGTGT

TTCCTCTGGCCCCATCTAGCAAGAGCACATCCGGAGGCACCGCCGCCCT

GGGATGTCTGGTGAAGGATTACTTCCCAGAGCCCGTGACCGTGTCTTGG

AACAGCGGCGCCCTGACATCCGGAGTGCACACCTTTCCAGCCGTGCTGC

AGTCCTCTGGCCTGTACAGCCTGAGCTCCGTGGTGACAGTGCCTTCTAG

CTCCCTGGGCACACAGACCTATATCTGCAACGTGAATCACAAGCCCAGC

AATACCAAGGTGGACAAGAAGGTGGAGCCTAAGTCCTGTGATAAGACAC

ACACCTGCCCACCATGTCCTGCACCAGAGCTGCTGGGAGGACCATCCGT

GTTCCTGTTTCCTCCAAAGCCCAAGGACACACTGATGATCTCTCGCACA

CCCGAGGTGACCTGCGTGGTGGTGGACGTGAGCCACGAGGATCCTGAGG

TGAAGTTCAACTGGTACGTGGATGGCGTGGAGGTGCACAATGCCAAGAC

CAAGCCTAGAGAGGAGCAGTACAACAGCACATATCGGGTGGTGTCCGTG

CTGACCGTGCTGCACCAGGACTGGCTGAACGGCAAGGAGTATAAGTGCA

AGGTGTCCAATAAGGCCCTGCCCGCCCCTATCGAGAAGACAATCTCTAA

GGCAAAGGGACAGCCAAGGGAGCCTCAGGTGTACACCCTGCCCCCTTCC

AGGGAGGAGATGACAAAGAACCAGGTGTCTCTGACCTGTCTGGTGAAGG

GCTTCTATCCTTCCGACATCGCCGTGGAGTGGGAGTCTAATGGCCAGCC

AGAGAACAATTACAAGACCACACCACCCGTGCTGGACTCCGATGGCTCT

TTCTTTCTGTATTCTAAGCTGACCGTGGATAAGAGCAGATGGCAGCAGG

GCAACGTGTTTTCTTGTAGCGTGATGCACGAGGCCCTGCACAATCACTA

CACACAGAAGTCCCTGTCTCTGAGCCCAGGCAAGAGGAAGAGGAGAGCA

CGAGGCCCTGCACAATCACTACACACAGAAGTCCCTGTCTCTGAGCCCA

GGCAAGAGGAAGAGGAGATCCGGATCTGGAGCACCAGTGAAGCAGACCC

TGAACTTCGACCTGCTGAAGCTGGCCGGCGATGTGGAGAGCAATCCAGG

CCCCATGGCCACAGGCAGCAGAACCTCCCTGCTGCTGGCCTTTGGCCTG

CTGTGCCTGCCATGGCTGCAGGAGGGAAGCGCCGACATCCAGATGACCC

AGTCCCCATCTAGCCTGAGCGCCTCCATCGGCGATCGGGTGACAATCAC

CTGTCGCCCCTCCCAGAACATCAGGTCTTTCCTGAATTGGTTTCAGCAC

AAGCCAGGCAAGGCCCCCAAGCTGCTGATCTACGCAGCATCTAACCTGC

AGAGCGGCGTGCCATCCCGCTTCTCTGGAAGCGGATCCGGCACAGAGTT

TACACTGACCATCAGGTCCCTGCAGCCCGAGGACTTCGCCACCTACTAT

TGCCAGCAGAGCTATAACACACCTCCAACCTTTGGCCAGGGCACAAAGG

TGGAGATCAAGGGACAGCCTAAGGCAGCACCATCCGTGACCCTGTTCCC

ACCTTCCTCTGAGGAGCTGCAGGCCAATAAGGCCACCCTGGTGTGCCTG

ATCAGCGACTTTTACCCTGGAGCAGTGACCGTGGCATGGAAGGCCGATA

GCTCCCCTGTGAGGCCGGCGTGGAGACAACAACCCCATCTAAGCAGAGC

AACAATAAGTACGCCGCCTCTAGCTATCTGTCTCTGACCCCAGAGCAGT

GGAAGAGCCACCGGTCTTATAGCTGTCAGGTGACCCATGAAGGCTCAAC

TGTGGAGAAAACCGTCGCCCCAACTGAATGTTCCTAA

SEQ ID NO: 2 (nucleotide sequence for a codon optimized for miRNA against RNA polymerase, nucleoprotein, and hemagglutinin, each of which is a target, viral-specific protein)

CTGGAGGCTTGCTGAAGGCTGTATGCTGAAGGATCTTATTTCTTCGGAG

AGTTTTGGCCTCTGACTGACTTTCCGAAGATAAGATCCTTCAGGACACA

AGGCCTGTTACTAGCACTCACATGGAACAAATGGCCTCTAGCCTGGAGG

CTTGCTGAAGGCTGTATGCTGGAAGCAATTGAGGAGTGCCTAAGTTTTG

GCCTCTGACTGACTTAGGCACTTCAATTGCTTCCAGGACACAAGGCCTG

-continued

```
TTACTAGCACTCACATGGAACAAATGGCCTCTAGCCTGGAGGCTTGCTG
AAGGCTGTATGCTGTGAAGATCTGTTCCACCATTGAGTTTTGGCCTCTG
ACTGACTTAATGGTGACAGATCTTCACAGGACACAAGGCCTGTTACTAG
CACTCACATGGAACAAATGGCCTC
```

SEQ ID NO: 3 (AAV expression cassette with SEQ ID 1 and SEQ ID 2 inserted)

```
CAGCAGCTGCGCGCTCGCTCGCTCACTGAGGCCGCCCGGGCAAAGCCCG
GGCGTCGGGCGACCTTTGGTCGCCCGGCCTCAGTGAGCGAGCGAGCGCG
CAGAGAGGGAGTGGCCAACTCCATCACTAGGGGTTCCTTGTAGTTAATG
ATTAACCCGCCATGCTACTTATCTACGTAGCCATGCTCTAGGACATTGA
TTATTGACTAGTGGAGTTCCGCGTTACATAACTTACGGTAAATGGCCCG
CCTGGCTGACCGCCCAACGACCCCCGCCCATTGACGTCAATAATGACGT
ATGTTCCCATAGTAACGCCAATAGGGACTTTCCATTGACGTCAATGGGT
GGAGTATTTACGGTAAACTGCCCACTTGGCAGTACATCAAGTGTATCAT
ATGCCAAGTACGCCCCCTATTGACGTCAATGACGGTAAATGGCCCGCCT
GGCATTATGCCCAGTACATGACCTTATGGGACTTTCCTACTTGGCAGTA
CATCTACGTATTAGTCATCGCTATTACCATGGTCGAGGTGAGCCCCACG
TTCTGCTTCACTCTCCCCATCTCCCCCCCCTCCCCACCCCCAATTTTGT
ATTTATTTATTTTTTAATTATTTTGTGCAGCGATGGGGGCGGGGGGGGG
GGGGGGCGCGCGCCAGGCGGGGCGGGGCGGGGCGAGGGGCGGGGCGGGG
CGAGGCGGAGAGGTGCGGCGGCAGCCAATCAGAGCGGCGCGCTCCGAAA
GTTTCCTTTTATGGCGAGGCGGCGGCGGCGGCGGCCCTATAAAAAGCGA
AGCGCGCGGCGGGCGGGAGTCGCTGCGCGCTGCCTTCGCCCCGTGCCCC
GCTCCGCCGCCGCCTCGCGCCGCCCGCCCCGGCTCTGACTGACCGCGTT
ACTAAAACAGGTAAGTCCGGCCTCCGCGCCGGGTTTTGGCGCCTCCCGC
GGGCGCCCCCCTCCTCACGGCGAGCGCTGCCACGTCAGACGAAGGGCGC
AGCGAGCGTCCTGATCCTTCCGCCCGGACGCTCAGGACAGCGGCCCGCT
GCTCATAAGACTCGGCCTTAGAACCCCAGTATCAGCAGAAGGACATTTT
AGGACGGGACTTGGGTGACTCTAGGGCACTGGTTTTCTTTCCAGAGAGC
GGAACAGGCGAGGAAAAGTAGTCCCTTCTCGGCGATTCTGCGGAGGGAT
CTCCGTGGGCGGTGAACGCCGATGATGCCTCTACTAACCATGTTCATG
TTTTCTTTTTTTTCTACAGGTCCTGGGTGACGAACAGGGTACCGCCAC
CATGGCTACTGGGTCAAGAACATCTCTGCTGCTGGCTTTCGGGCTGCTG
TGCCTGCCTTGGCTGCAGGAGGGAGTGCTCAGGTCCAGCTGCAGGAGA
GCGGACCAGGCCTGGTGAAGCCTTCCGAGACACTGTCTCTGACCTGCTC
CGTGTCTGGCGTGTCCGTGACATCTGACATCTACTATTGGACCTGGATC
AGGCAGCCACCTGGCAAGGGCTGGAGTGGATCGGCTACATCTTCTATA
ACGGCGACACCAACTACAATCCCAGCCTGAAGTCCAGAGTGACAATGAG
CATCGATACCTCCAAGAATGAGTTCTCTCTGAGGCTGACAAGCGTGACC
GCAGCAGACACAGCCGTGTACTTTTGCGCCAGGGGCACCGAGGATCTGG
```

```
GCTATTGCAGCTCCGGCTCCTGTCCTAACCACTGGGGCCAGGGCACACT
GGTGACCGTGTCTAGCTCCACAAAGGGCCCAAGCGTGTTTCCTCTGGCC
CCATCTAGCAAGAGCACATCCGGAGGCACCGCCGCCCTGGGATGTCTGG
TGAAGGATTACTTCCCAGAGCCCGTGACCGTGTCTTGGAACAGCGGCGC
CCTGACATCCGGAGTGCACACCTTTCCAGCCGTGCTGCAGTCCTCTGGC
CTGTACAGCCTGAGCTCCGTGGTGACAGTGCCTTCTAGCTCCCTGGGCA
CACAGACCTATATCTGCAACGTGAATCACAAGCCCAGCAATACCAAGGT
GGACAAGAAGGTGGAGCCTAAGTCCTGTGATAAGACACACCTGCCCA
CCATGTCCTGCACCAGAGCTGCTGGGAGGACCATCCGTGTTCCTGTTTC
CTCCAAAGCCCAAGGACACACTGATGATCTCTCGCACACCCGAGGTGAC
CTGCGTGGTGGTGGACGTGAGCCACGAGGATCCTGAGGTGAAGTTCAAC
TGGTACGTGGATGGCGTGGAGGTGCACAATGCCAAGACCAAGCCTAGAG
AGGAGCAGTACAACAGCACATATCGGGTGGTGTCCGTGCTGACCGTGCT
GCACCAGGACTGGCTGAACGGCAAGGAGTATAAGTGCAAGGTGTCCAAT
AAGGCCCTGCCCGCCCCTATCGAGAAGACAATCTCTAAGGCAAAGGGAC
AGCCAAGGGAGCCTCAGGTGTACACCCTGCCCCCTTCCAGGGAGGAGAT
GACAAAGAACCAGGTGTCTCTGACCTGTCTGGTGAAGGGCTTCTATCCT
TCCGACATCGCCGTGGAGTGGGAGTCTAATGGCCAGCCAGAGAACAATT
ACAAGACCACACCACCCGTGCTGGACTCCGATGGCTCTTTCTTTCTGTA
TTCTAAGCTGACCGTGGATAAGAGCAGATGGCAGCAGGGCAACGTGTTT
TCTTGTAGCGTGATGCACGAGGCCCTGCACAATCACTACACACAGAAGT
CCCTGTCTCTGAGCCCAGGCAAGAGGAAGAGGAGATCCGGATCTGGAGC
ACCAGTGAAGCAGACCCTGAACTTCGACCTGCTGAAGCTGGCCGGCGAT
GTGGAGAGCAATCCAGGCCCCATGGCCACAGGCAGCAGAACCTCCCTGC
TGCTGGCCTTTGGCCTGCTGTGCCTGCCATGGCTGCAGGAGGGAAGCGC
CGACATCCAGATGACCCAGTCCCCATCTAGCCTGAGCGCCTCCATCGGC
GATCGGGTGACAATCACCTGTCGCCCCTCCCAGAACATCAGGTCTTTCC
TGAATTGGTTTCAGCACAAGCCAGGCAAGGCCCCCAAGCTGCTGATCTA
CGCAGCATCTAACCTGCAGAGCGGCGTGCCATCCCGCTTCTCTGGAAGC
GGATCCGGCACAGAGTTTACACTGACCATCAGGTCCCTGCAGCCCGAGG
ACTTCGCCACCTACTATTGCCAGCAGAGCTATAACACACCTCCAACCTT
TGGCCAGGGCACAAAGGTGGAGATCAAGGGACAGCCTAAGGCAGCACCA
TCCGTGACCCTGTTCCCACCTTCCTCTGAGGAGCTGCAGGCCAATAAGG
CCACCCTGGTGTGCCTGATCAGCGACTTTTACCCTGGAGCAGTGACCGT
GGCATGGAAGGCCGATAGCTCCCCTGTGAAGGCCGGCGTGGAGACAACA
ACCCCATCTAAGCAGAGCAACAATAAGTACGCCGCCTCTAGCTATCTGT
CTCTGACCCCAGAGCAGTGGAAGAGCCACCGGTCTTATAGCTGTCAGGT
GACCCATGAAGGCTCAACTGTGGAGAAAACCGTCGCCCCAACTGAATGT
TCCTAATCTAGACGAGCTCGGTACCTCTAGATGCTGGAGGCTTGCTGAA
GGCTGTATGCTGAAGGATCTTATTTCTTCGGAGAGTTTTGGCCTCTGAC
TGACTTTCCGAAGATAAGATCCTTCAGGACACAAGGCCTGTTACTAGCA
```

-continued

CTCACATGGAACAAATGGCCTCTAGCCTGGAGGCTTGCTGAAGGCTGTA

TGCTGGAAGCAATTGAGGAGTGCCTAAGTTTTGGCCTCTGACTGACTTA

GGCACTTCAATTGCTTCCAGGACACAAGGCCTGTTACTAGCACTCACAT

GGAACAAATGGCCTCTAGCCTGGAGGCTTGCTGAAGGCTGTATGCTGTG

AAGATCTGTTCCACCATTGAGTTTTGGCCTCTGACTGACTTAATGGTGA

CAGATCTTCACAGGACACAAGGCCTGTTACTAGCACTCACATGGAACAA

ATGGCCTCTCTAGAAAGCTTCGTCTAGAATAATCAACCTCTGGATTACA

AAATTTGTGAAAGATTGACTGGTATTCTTAACTATGTTGCTCCTTTTAC

GCTATGTGGATACGCTGCTTTAATGCCTTTGTATCATGCTATTGCTTCC

CGTATGGCTTTCATTTTCTCCTCCTTGTATAAATCCTGGTTGCTGTCTC

TTTATGAGGAGTTGTGGCCCGTTGTCAGGCAACGTGGCGTGGTGTGCAC

TGTGTTTGCTGACGCAACCCCCACTGGTTGGGGCATTGCCACCACCTGT

CAGCTCCTTTCCGGGACTTTCGCTTTCCCCCTCCCTATTGCCACGGCGG

AACTCATCGCCGCCTGCCTTGCCCGCTGCTGGACAGGGGCTCGGCTGTT

GGGCACTGACAATTCCGTGGTGTTGTCGGGGAAATCATCGTCCTTTCCT

TGGCTGCTCGCCTGTGTTGCCACCTGGATTCTGCGCGGGACGTCCTTCT

GCTACGTCCCTTCGGCCCTCAATCCAGCGGACCTTCCTTCCCGCGGCCT

GCTGCCGGCTCTGCGGCCTCTTCCGCGTCTTCGCCTTCGCCCTCAGACG

AGTCGGATCTCCCTTTGGGCCGCCTCCCCGCCTAAGCTTATCGATACCG

TCGAGATCTAACTTGTTTATTGCAGCTTATAATGGTTACAAATAAAGCA

ATAGCATCACAAATTTCACAAATAAAGCATTTTTTTCACTGCATTCTAG

TTGTGGTTTGTCCAAACTCATCAATGTATCTTATCATGTCTGGATCTCG

ACCTCGACTAGAGCATGGCTACGTAGATAAGTAGCATGGCGGGTTAATC

ATTAACTACAAGGAACCCCTAGTGATGGAGTTGGCCACTCCCTCTCTGC

GCGCTCGCTCGCTCACTGAGGCCGGGCGACCAAAGGTCGCCCGACGCCC

GGGCTTTGCCCGGGCGGCCTCAGTGAGCGAGCGAGCGCGCAGCTGGCGT

AATAGCGAAGAGGCCCGCACCGATCGCCCTTCCCAACAGTTGCGCAGCC

TGAATGGCGAATGGCGATTCCGTTGCAATGGCTGGCGGTAATATTGTTC

TGGATATTACCAGCAAGGCCGATAGTTTGAGTTCTTCTACTCAGGCAAG

TGATGTTATTACTAATCAAAGAAGTATTGCGACAACGGTTAATTTGCGT

GATGGACAGACTCTTTTACTCGGTGGCCTCACTGATTATAAAAACACTT

CTCAGGATTCTGGCGTACCGTTCCTGTCTAAAATCCCTTTAATCGGCCT

CCTGTTTAGCTCCCGCTCTGATTCTAACGAGGAAAGCACGTTATACGTG

CTCGTCAAAGCAACCATAGTACGCGCCCTGTAGCGGCGCATTAAGCGCG

GCGGGTGTGGTGGTTACGCGCAGCGTGACCGCTACACTTGCCAGCGCCC

TAGCGCCCGCTCCTTTCGCTTTCTTCCCTTCCTTTCTCGCCACGTTCGC

CGGCTTTCCCCGTCAAGCTCTAAATCGGGGGCTCCCTTTAGGGTTCCGA

TTTAGTGCTTTACGGCACCTCGACCCCAAAAAACTTGATTAGGGTGATG

GTTCACGTAGTGGGCCATCGCCCTGATAGACGGTTTTTCGCCCTTTGAC

GTTGGAGTCCACGTTCTTTAATAGTGGACTCTTGTTCCAAACTGGAACA

-continued

ACACTCAACCCTATCTCGGTCTATTCTTTTGATTATAAGGGATTTTGC

CGATTTCGGCCTATTGGTTAAAAAATGAGCTGATTTAACAAAAATTTAA

CGCGAATTTTAACAAAATATTAACGTTTACAATTTAAATATTTGCTTAT

ACAATCTTCCTGTTTTTGGGGCTTTTCTGATTATCAACCGGGGTACATA

TGATTGACATGCTAGTTTTACGATTACCGTTCATCGATTCTCTTGTTTG

CTCCAGACTCTCAGGCAATGACCTGATAGCCTTTGTAGAGACCTCTCAA

AAATAGCTACCCTCTCCGGCATGAATTTATCAGCTAGAACGGTTGAATA

TCATATTGATGGTGATTTGACTGTCTCCGGCCTTTCTCACCCGTTTGAA

TCTTTACCTACACATTACTCAGGCATTGCATTTAAAATATATGAGGGTT

CTAAAAATTTTTATCCTTGCGTTGAAATAAAGGCTTCTCCCGCAAAAGT

ATTACAGGGTCATAATGTTTTGGTACAACCGATTTAGCTTTATGCTCT

GAGGCTTTATTGCTTAATTTTGCTAATTCTTTGCCTTGCCTGTATGATT

TATTGGATGTTGGAATTCCTGATGCGGTATTTTCTCCTTACGCATCTGT

GCGGTATTTCACACCGCATATGGTGCACTCTCAGTACAATCTGCTCTGA

TGCCGCATAGTTAAGCCAGCCCCGACACCCGCCAACACCCGCTGACGCG

CCCTGACGGGCTTGTCTGCTCCCGGCATCCGCTTACAGACAAGCTGTGA

CCGTCTCCGGGAGCTGCATGTGTCAGAGGTTTTCACCGTCATCACCGAA

ACGCGCGAGACGAAAGGGCCTCGTGATACGCCTATTTTTATAGGTTAAT

GTCATGATAATAATGGTTTCTTAGACGTCAGGTGGCACTTTTCGGGGAA

ATGTGCGCGGAACCCCTATTTGTTTATTTTTCTAAATACATTCAAATAT

GTATCCGCTCATGAGACAATAACCCTGATAAATGCTTCAATAATATTGA

AAAAGGAAGAGTATGAGTATTCAACATTTCCGTGTCGCCCTTATTCCCT

TTTTTGCGGCATTTTGCCTTCCTGTTTTTGCTCACCCAGAAACGCTGGT

GAAAGTAAAAGATGCTGAAGATCAGTTGGGTGCACGAGTGGGTTACATC

GAACTGGATCTCAACAGCGGTAAGATCCTTGAGAGTTTTCGCCCCGAAG

AACGTTTTCCAATGATGAGCACTTTTAAAGTTCTGCTATGTGGCGCGGT

ATTATCCCGTATTGACGCCGGGCAAGAGCAACTCGGTCGCCGCATACAC

TATTCTCAGAATGACTTGGTTGAGTACTCACCAGTCACAGAAAAGCATC

TTACGGATGGCATGACAGTAAGAGAATTATGCAGTGCTGCCATAACCAT

GAGTGATAACACTGCGGCCAACTTACTTCTGACAACGATCGGAGGACCG

AAGGAGCTAACCGCTTTTTTGCACAACATGGGGGATCATGTAACTCGCC

TTGATCGTTGGGAACCGGAGCTGAATGAAGCCATACCAAACGACGAGCG

TGACACCACGATGCCTGTAGCAATGGCAACAACGTTGCGCAAACTATTA

ACTGGCGAACTACTTACTCTAGCTTCCCGGCAACAATTAATAGACTGGA

TGGAGGCGGATAAAGTTGCAGGACCACTTCTGCGCTCGGCCCTTCCGGC

TGGCTGGTTTATTGCTGATAAATCTGGAGCCGGTGAGCGTGGGTCTCGC

GGTATCATTGCAGCACTGGGGCCAGATGGTAAGCCCTCCCGTATCGTAG

TTATCTACACGACGGGGAGTCAGGCAACTATGGATGAACGAAATAGACA

GATCGCTGAGATAGGTGCCTCACTGATTAAGCATTGGTAACTGTCAGAC

CAAGTTTACTCATATATACTTTAGATTGATTTAAAACTTCATTTTTAAT

TTAAAAGGATCTAGGTGAAGATCCTTTTTGATAATCTCATGACCAAAAT

-continued

CCCTTAACGTGAGTTTTCGTTCCACTGAGCGTCAGACCCCGTAGAAAAG

ATCAAAGGATCTTCTTGAGATCCTTTTTTTCTGCGCGTAATCTGCTGCT

TGCAAACAAAAAAACCACCGCTACCAGCGGTGGTTTGTTTGCCGGATCA

AGAGCTACCAACTCTTTTTCCGAAGGTAACTGGCTTCAGCAGAGCGCAG

ATACCAAATACTGTCCTTCTAGTGTAGCCGTAGTTAGGCCACCACTTCA

AGAACTCTGTAGCACCGCCTACATACCTCGCTCTGCTAATCCTGTTACC

AGTGGCTGCTGCCAGTGGCGATAAGTCGTGTCTTACCGGGTTGGACTCA

AGACGATAGTTACCGGATAAGGCGCAGCGGTCGGGCTGAACGGGGGGTT

CGTGCACACAGCCCAGCTTGGAGCGAACGACCTACACCGAACTGAGATA

CCTACAGCGTGAGCTATGAGAAAGCGCCACGCTTCCCGAAGGGAGAAAG

GCGGACAGGTATCCGGTAAGCGGCAGGGTCGGAACAGGAGAGCGCACGA

GGGAGCTTCCAGGGGGAAACGCCTGGTATCTTTATAGTCCTGTCGGGTT

TCGCCACCTCTGACTTGAGCGTCGATTTTTGTGATGCTCGTCAGGGGGG

CGGAGCCTATGGAAAAACGCCAGCAACGCGGCCTTTTTACGGTTCCTGG

CCTTTTGCTGGCCTTTTGCTCACATGTTCTTTCCTGCGTTATCCCTGA

TTCTGTGGATAACCGTATTACCGCCTTTGAGTGAGCTGATACCGCTCGC

CGCAGCCGAACGACCGAGCGCAGCGAGTCAGTGAGCGAGGAAGCGGAAG

AGCGCCCAATACGCAAACCGCCTCTCCCCGCGCGTTGGCCGATTCATTA

ATG

Example 1—Expression Cassette

Expression cassettes for expression of a monoclonal antibody (mAb) and/or miRNA were synthesized by Genscript. Each cassette contained a signal peptide, and/or the variable heavy domain, the human IgG1 constant domain, and/or the miRNA sequence followed by (when it is an Ab), a self-cleaving 2A peptide sequence, a signal peptide, the variable light domain and the human lambda constant domain. The synthesized mAb and/or miRNA expression cassettes were cloned into the pAVA-00200 plasmid backbone containing the CASI promoter1, multiple cloning site (MCS), Woodchuck Hepatitis Virus post-transcriptional regulatory element (WPRE), Simian virus 40 (SV40) polyadenylation (polyA) sequence all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each mAb and/or protein and/or miRNA expression cassette was amplified by PCR using Taq polymerase and the PCR products were gel purified and the bands on interest were also excised and purified using a gel extraction kit. These PCR products contained the mAb and/or protein and/or miRNA expression cassettes in addition to 15 base pair 5' and 3' overhangs that align with the ends of the linearized pAVA-00200 backbone. Using in-fusion cloning2, the amplified mAb or protein or miRNA expression cassettes are integrated with the pAVA-00200 backbone via homologous recombination. The resulting plasmid vectors contained the following: 5' ITR, CASI promoter, and/or mAb expression cassette, and/or miRNA expression cassette, WPRE, SV40 polyA and ITR 3'.

Example 2—Animal Studies

Female BALB/c mice were purchased from Charles River. AAV vectors that included a nucleotide sequence causing expression of an ALP that encodes for production of ALP-Flu20 (Vector 1 that includes SEQ ID No: 1), three sequences of miRNA that bind to and cause degradation of target, viral-specific proteins miRNA's (Vector 2 that includes SEQ ID NO: 2 and that targets the mRNA of each of RNA polymerase, nucleoprotein, and hemagglutinin), or both of the ALP and the three miRNAs (Vector 3 that includes SEQ ID NO: 3), as in Example 1, were administered to 6-week-old BALB/c mice. All animal experiments were approved by the institutional animal care committees of the Canadian Science Centre for Human and Animal Health and the University of Guelph. Intranasal administration of the AAV vectors were performed using a 40-μL injection volume. The dose used was about $2\times10^{11}$ vector genomes per mouse. After four weeks the mice were infected intra-nasally with influenza A strain PR8. The viral dose used was $1\times10^{5}$ plaque forming units (PFUs).

Example 3—Experimental Data

FIG. 1 presents the data, in the form of a Kaplan-Meir graph, obtained from mice that received an intranasal administration of a sham carrier (control, shown as 10 in FIG. 1) or one of Vector 1 (shown as 12 in FIG. 1, Vector 2 (shown as 14 in FIG. 1) or Vector 3 (shown as 16 in FIG. 1) followed by intranasal administration influenza A strain PR8.

As shown in FIG. 1, the group of mice that received Vector 3 (that included sequences that encoded for increased production of ALP and miRNA against the mRNA of three target, viral-specific proteins) demonstrated statistically significant higher survival (p=0.007) than the group of control mice, the group of mice that received Vector 1 and the group of mice that received Vector 2.

Without being bound by any particular theory, the embodiments of the present disclosure that cause a subject to increase production of both the ALP and the one or more miRNA sequences can be used to treat a subject who is infected with a target virus. It is understood that the description and examples provided herein refer to one given target virus, namely influenza A, yet the embodiments of the present disclosure are not limited to just the one exemplary, target virus. For example, a member of the Orthomyxoviridae family of viruses can be a target protein but members of other virus families can also be the target virus. Because the ALP can be designed to target and/or recognize any known surface-protein of any virus and because each of the one or more sequences of miRNA can be designed to be complementary to any known target, viral-specific protein, the embodiments of the present disclosure can be designed for any target virus with at least one known surface protein and at least one target, virus-specific protein with a known mRNA nucleotide sequence.

The invention claimed is:

1. A method of treating a subject with a condition, the method comprising a step of administering to the subject a therapeutic dose of a composition that comprises a recombinant plasmid (RP) with a sequence of nucleotides that comprise a start region, an end region and an insert positioned between the start region and the end region, wherein the insert encodes for production of an antibody-like protein (ALP) that is bindable with a surface protein of an influenza virus and a further sequence of micro-interfering ribonucleic acid (miRNA) that binds to and causes degradation of messenger ribonucleic acid (mRNA) that encodes for a target, viral protein of the influenza virus,
   wherein the sequence of nucleotides of the insert comprises:
   i) a sequence that comprises SEQ ID No: 1, and
   ii) the further sequence that comprises SEQ ID No: 2.

2. The method of claim 1, wherein the condition is an infection of the influenza virus.

* * * * *